US007560275B2

(12) United States Patent
Vacanti et al.

(10) Patent No.: US 7,560,275 B2
(45) Date of Patent: *Jul. 14, 2009

(54) COMPOSITIONS AND METHODS FOR GENERATING SKIN

(75) Inventors: Martin P. Vacanti, Westborough, MA (US); Charles A. Vacanti, Uxbridge, MA (US)

(73) Assignee: VBI Technologies, L.L.C., Houston, TX (US)

( * ) Notice: Subject to any disclaimer, the term of this patent is extended or adjusted under 35 U.S.C. 154(b) by 913 days.

This patent is subject to a terminal disclaimer.

(21) Appl. No.: 10/379,394

(22) Filed: Mar. 3, 2003

(65) Prior Publication Data

US 2004/0033598 A1 Feb. 19, 2004

Related U.S. Application Data

(63) Continuation of application No. 09/475,611, filed on Dec. 30, 1999, now abandoned.

(51) Int. Cl.
*C12N 5/00* (2006.01)
(52) U.S. Cl. ........................................ 435/325; 435/375
(58) Field of Classification Search .................. 435/243
See application file for complete search history.

(56) References Cited

U.S. PATENT DOCUMENTS

| 4,060,081 A | | 11/1977 | Yannas et al. |
| 4,149,936 A | * | 4/1979 | Messing et al. ............. 435/176 |
| 4,191,747 A | | 3/1980 | Scheicher |
| 4,846,835 A | | 7/1989 | Grande |
| 4,997,443 A | | 3/1991 | Walthall et al. |
| 5,041,138 A | | 8/1991 | Vacanti et al. |
| 5,071,644 A | | 12/1991 | Viegas et al. |
| 5,082,670 A | | 1/1992 | Gage et al. |
| 5,126,141 A | | 6/1992 | Henry |
| 5,192,326 A | | 3/1993 | Bao et al. |
| 5,277,911 A | | 1/1994 | Viegas et al. |
| 5,292,516 A | | 3/1994 | Viegas et al. |
| 5,292,655 A | * | 3/1994 | Wille, Jr. .................... 435/384 |
| 5,294,446 A | | 3/1994 | Schlameus et al. |
| 5,298,260 A | | 3/1994 | Viegas et al. |
| 5,300,295 A | | 4/1994 | Viegas et al. |
| 5,306,501 A | | 4/1994 | Viegas et al. |
| 5,318,780 A | | 6/1994 | Viegas et al. |
| 5,405,366 A | | 4/1995 | Fox et al. |
| 5,410,016 A | | 4/1995 | Hubbell et al. |
| 5,411,883 A | * | 5/1995 | Boss et al. ..................... 435/29 |
| 5,443,950 A | | 8/1995 | Naughton et al. |
| 5,512,600 A | | 4/1996 | Mikos et al. |
| 5,514,378 A | | 5/1996 | Mikos et al. |
| 5,514,379 A | * | 5/1996 | Weissleder et al. .......... 424/426 |
| 5,523,226 A | * | 6/1996 | Wheeler ...................... 435/325 |
| 5,529,914 A | | 6/1996 | Hubbell et al. |
| 5,567,612 A | | 10/1996 | Vacanti et al. |
| 5,575,815 A | | 11/1996 | Slepian et al. |
| 5,578,485 A | | 11/1996 | Naughton et al. |
| 5,589,376 A | | 12/1996 | Anderson et al. |
| 5,593,974 A | | 1/1997 | Rosenberg et al. |
| 5,667,778 A | | 9/1997 | Atala |
| 5,696,175 A | | 12/1997 | Mikos et al. |
| 5,709,854 A | | 1/1998 | Griffith-Cima et al. |
| 5,716,404 A | | 2/1998 | Vacanti et al. |
| 5,736,372 A | | 4/1998 | Vacanti et al. |
| 5,750,376 A | | 5/1998 | Weiss et al. |
| 5,753,506 A | | 5/1998 | Johe |
| 5,759,830 A | | 6/1998 | Vacanti et al. |
| 5,762,926 A | | 6/1998 | Gage et al. |
| 5,766,948 A | * | 6/1998 | Gage et al. ................... 435/368 |
| 5,770,193 A | | 6/1998 | Vacanti et al. |
| 5,770,417 A | | 6/1998 | Vacanti et al. |
| 5,780,300 A | | 7/1998 | Artavanis-Tsakonas et al. |
| 5,786,216 A | | 7/1998 | Dionne et al. |
| 5,795,790 A | | 8/1998 | Schinstine et al. |
| 5,800,811 A | | 9/1998 | Hall et al. |
| 5,804,178 A | | 9/1998 | Vacanti et al. |
| 5,827,735 A | | 10/1998 | Young et al. |
| 5,827,742 A | * | 10/1998 | Scadden ...................... 435/377 |
| 5,830,651 A | | 11/1998 | Cauley et al. |
| 5,834,029 A | | 11/1998 | Bellamkonda et al. |
| 5,851,832 A | | 12/1998 | Weiss et al. |
| 5,855,610 A | | 1/1999 | Vacanti et al. |
| 5,994,754 A | | 11/1999 | Hayashi et al. |

FOREIGN PATENT DOCUMENTS

| EP | 0 361 957 | 4/1990 |
| WO | WO 93/16687 | 2/1993 |
| WO | WO 93/24627 | 12/1993 |
| WO | WO 94/25079 | 11/1994 |
| WO | WO 94/25080 | 11/1994 |
| WO | WO 96/40304 | 12/1996 |
| WO | WO 97/41208 | 11/1997 |
| WO | WO 98/23761 | 6/1998 |
| WO | WO 98/30678 | 7/1998 |

OTHER PUBLICATIONS

Pittenger MF et al. 1999. Multilineage potential of adult human mesenchymal stem cells. Science 284: 143-147.*
Vacanti MP et al. 2001. Identification and initial characterization of spore-like cells in adult mammals. J Cell Biochem 80: 455-460.*
Random House Webster's College Dictionary definition of "spore." 1991. New York: Random House. p. 1294.*
Young, HE. "Stem cells and tissue engineering." in Huard J et al. Gene therapy and tissue engineering in orthopedic and sports medicine (2000, Birkhaueser, Boston MA). pp. 149-150.*
Burke et al., "Successful use of a physiologically acceptable artificial skin in the treatment of extensive burn injury," *Ann. Surg.* 194:413-428 (1981).
Cornelius et al., "In vitro-generation of islets in long-term cultures of pluripotent stem cells from adult mouse pancreas," *Horm. Metab. Res.* 29:271-277 (1997).

(Continued)

*Primary Examiner*—L E Barnhart
(74) *Attorney, Agent, or Firm*—Pabst Patent Group LLP (57) ABSTRACT

Compositions and methods for growing new skin, which can be used to repair or replace skin that has been damaged or removed by a variety of insults.

23 Claims, 5 Drawing Sheets

OTHER PUBLICATIONS

Craig et al., "In Vivo Growth Factor Expansion of Endogenous Subependymal Neural Precursor Cell Populations in the Adult Mouse Brain," *The Journal Of Neuroscience* 16:2649-2658 (1996).

Davis et al., "A Self-Renewing Multipotential Stem Cell in Embryonic Rat Cerebral Cortex," *Nature* 372:263-269 (1994).

Farriol et al., "Epidermal growth factor excretion in burned rats," *Burns* 20:496-498 (1994).

Frederiksen et al., "Proliferation and Differentiation of Rat Neuroepithelial Precursor Cells In Vivo," *The Journal Of Neuroscience* 8:1144-1151 (1988).

Ferringa et al., "Regeneration of Corticospinal Axons in the Rat," *Annals Of Neurology*, 2:315-321 (1977).

Gage et al., "Survival and Differentiation of Adult Neuronal Progenitor Cells Transplanted to the Adult Brain," *Proc. Natl. Acad. Sci. USA*, 92:11879-11883 (1995).

Hansbrough, "Current status of skin replacements for coverage of extensive burn wounds," *J. Trauma* 30(12):S155-S162 (1992).

Houle et al., "Bridging a Complete Transection Lesion of Adult Rat Spinal Cord with Growth Factor-Treated Nitrocellulose Implants," *Journal Of Neural Transplantation & Plasticity*, 5:115-124 (1994).

Lachyankar et al., "Embryonic Precursor Cells that Express Trk Receptors: Induction of Different Cells Fates by NGF, BDNF, NT-3, and CNTF," *Experimental Neurology* 144:350-360 (1997).

Lindsell et al., "Jagged: a mammalian ligand that activates Notch-1," *Cell* 80:909-917 (1997).

Moller et al., "Differential expression of neural cell adhesion molecule and cadherins in pancreatic islets, glucagonomas, and insulinomas," *Mol. Endocrinology* 6:1332-1342 (1992).

Moore et al., "Vascular function and tissue injury in murine skin following hyperthermia and photodynamic therapy, alone and in combination," *Br. J. Cancer* 66:1037-1043 (1992).

Morshead et al., "Neural Stem Cells in the Adult Mammalian Forebrain: A Relatively Quiescent Subpopulation of Subependymal Cells," *Neuron* 13:1071-1082 (1994).

Raszka et al., "The use of hyaluronidase in the treatment of intravenous extravasation injuries," *J. Perinatol.* 10:146-149 (1990).

Ray et al., "Proliferation, Differentiation, and Long-Term Culture of Primary Hippocampal Neurons," *Proc. Natl. Acad. Sci. USA* 90:3602-3606 (1993).

Ray et al., "Spinal Cord Neuroblasts Proliferate in Response to Basic Fibroblast Growth Factor," *The Journal Of Neuroscience* 14:35483564 (1994).

Reynolds et al., "Clonal and Population Analyses Demostrate that an EGF-Responsive Mammalian Embryonic CNS Precursor is a Stem Cell," *Developmental Biology* 175:1-13 (1996).

Reynolds et al., "Generation of Neurons and Astrocytes from Isolated Cells of the Adult Mammalian Central Nervous System," *Science* 255:1707-1710 (1992).

Reynolds et al., "A Multipotent EGF-Responsive Striatal Embryonic Progenitor Cell Produces Neurons and Astrocytes," *The Journal Of Neuroscience* 12:4565-4574 (1992).

Shihabuddin et al., "The Adult CNS Retains the Potential to Direct Region-Specific Differentiation of a Transplanted Neuronal Precursor Cell Line," *The Journal Of Neuroscience* 15:6666-6678 (1995).

Shihabuddin et al., "Induction of Mature Neuronal Properties in Immortalized Neuronal Precursor Cells Following Grafting into the Neonatal CNS," *Journal Of Neurocytology* 25:101-111 (1996).

Stanton et al., "The Growth of Chondrocytes Using Gelfoam as a Biodegradable Scaffold," *Journal Of Materials Science: Materials In Medicine* 6:739-744 (1996).

Suhonen et al., "Differentiation of Adult Hippocampus-Derived Progenitors into Olfactory Neurons In Vivo," *Nature* 383:624-627 (1996).

Taylor et al., "Widespread Engraftment of Neural Progenitor and Stem-Like Cells Throughout the Mouse Brain," *Transplantation Proceedings* 29:845-847 (1997).

Teitelman et al., "Cells of mouse endocrine pancreas coexpress insulin, glucagon and the neuronal proteins tyrosine hydroxylase and neuropeptide Y, but not pancreatic polypeptide," *Development* 118:1031-1039 (1993).

Yannas et al., "Wound tissue can utilize a polymeric template to synthesize a functional extension of skin," *Science* 215:174-176 (1982).

Ferrari, et al., "Muscle regeneration by bone marrow-derived myogenic progenitors" *Science* 279: 1528-1530 (1998).

Gage, "Mammalian neural stem cells" *Science* 287: 1433-1438 (2000).

Jackson, et al., "Hematopoietic potential of stem cells isolated from murine skeletal muscle" *Proceedings of the National Academy of Sciences* 96(25): 14482-14486 (1999).

McDonald, et al., "Transplanted embryonic stem cells survive, differentiate and promote recovery in injured rat spinal cord" *Nature Medicine* 5(12): 1410-1412 (1999).

Mezey, et al., "Turing blood into brain: Cells bearing neuronal antigens generated in vivo from bone marrow" *Science* 290: 1779-1782 (2000).

Pittenger, et al., "Multilineage potential of adult human mesenchymal stem cells" *Science* 284: 143-147 (1999).

Prockop, "Marrow stromal cells as stem cells for nonhematopoietic tissues" *Science* 276: 71-74 (1997).

Tropepe, et al., "Retinal stem cells in the adult mammalian eye" *Science* 287: 2032-2036 (2000).

Weissman, "Translating stem and progenitor cell biology to the clinic; Barriers and opportunities" *Science* 287: 1442-1446 (2000).

\* cited by examiner

PRIOR ART

COMPOSITIONS AND METHODS FOR GENERATING SKIN

This application is a continuation of U.S. Ser. No. 09/475,611, which was filed On Dec. 30, 1999, now abandoned. The contents of U.S. Ser. No. 09/475,611 are hereby incorporated in their entirety.

FIELD OF THE INVENTION

The invention relates to compositions and methods for generating or repairing skin.

BACKGROUND OF THE INVENTION

Patients who have a birth defect, a disfiguring disease, or who have suffered a burn or other traumatic injury often need reconstructive surgery. These patients have benefited in recent years from tissue engineering, an emerging field in which new tissue is grown in culture and manipulated so that it forms a desired shape. For example, a damaged cartilage meniscus in a patient's knee can be replaced with an artificially engineered meniscus. See, for example, Vacanti et al. (U.S. Pat. No. 5,041,138). Similarly, hollow spaces or lumens within tissues can be filled with cells suspended in, for example, gelatin, collagen, fibrin, or various hydrogels. See, for example, Griffith-Cima et al. (International Patent Application WO 94/25080).

Methods to regenerate skin, which reach beyond traditional skin grafting, have also been described. For example, keratinocytes have been used to generate an epithelial layer of skin (see, e.g., Hansbrough, *J. Trauma*, 30(12):S155-S162, 1992). However, cultured keratinocyte sheets lack a dermal component, and this is a potentially serious deficiency for achieving a successful replacement for full-thickness skin (Hansbrough, supra). Moreover, the "skin" generated by this and other presently available methods is not normally pigmented (because there are insufficient melanocytes) and it does not contain important structures such as hair follicles, sweat glands, sebaceous glands, and nail beds.

SUMMARY OF THE INVENTION

The invention is based on the discovery that a life-like artificial skin can be produced by culturing spore-like cells or skin progenitor cells and allowing them, when applied to a living body or used in conjunction with present skin replacement methods, to differentiate into epidermal or dermal cells (including melanocytes) as well as into hair follicles, sweat glands, sebaceous glands, ganglia and similar adnexal structures.

Accordingly, the invention features isolated spore-like cells having the following characteristics. The cells are multipotent, i.e., they have the potential to differentiate into two or more cell types. For example, multipotent spore-like cells can differentiate into epithelial cells, keratinocytes, and melanocytes. The cell is also small, having a diameter of less than one to approximately seven microns (e.g., a diameter of one to two, two to four, three to five, or five to ten microns), and is tolerant of oxygen deprivation. Viable spore-like cells can survive in low-oxygen environments (such as those that exist within the tissues of a deceased animal) for many hours (e.g., four, six, ten, twelve, or 24 hours or more). Spore-like cells are surrounded by an outer membrane that is rich in glycolipids and mucopolysaccharides. In fact, there are sufficient glycolipids and mucopolysaccharides that the cells appear to have one or more dark stripes when viewed by transmission electron microscopy. When the cells are exceedingly small (e.g., less than one micron) the stripes are not as obvious but can nevertheless be seen with a trained eye. Electron micrographs and histological stains for nucleic acids reveal that a large portion (e.g., at least about 50% and up to 90% or more) of the volume of a spore-like cell is comprised of nucleic acids.

Spore-like cells can be obtained from various tissues, organs, and bodily fluids. For example, spore-like cells can be isolated from bodily fluids (e.g., blood or cerebrospinal fluid) of a post-natal animal (e.g., a mammal) or from solid organs such as the heart (or other muscle types, such as smooth or skeletal muscle), intestine, bladder, kidney, liver, lung, adrenal gland, skin, retina, or pancreas.

The invention also features spore-like cells having a diameter of less than approximately one micron (e.g., one-tenth to one-fifth of a micron) in diameter. A great deal of the volume of these cells is also comprised of nucleic acids (e.g., at least about half the volume of the cell and up to more than 90% of the cell can consist of nuclear material).

In another aspect, the invention features a method for isolating spore-like cells, which can be carried out by passing a tissue sample though a series of devices (e.g., size-exclusion devices such as pipettes or filters) having progressively smaller apertures (the smallest of which can be approximately 15μ). Smaller diameters (i.e., diameters smaller than 15μ) can also be used when more aggressive isolation is desired (i.e., when one desires fewer differentiated cells in the resulting culture). More aggressive isolation may be desired when one wishes to maintain the spore-like cells in their highly undifferentiated state. As described below, the conditions in which the cells are cultured can be such that their proliferation is encouraged and their differentiation is discouraged.

Cells of the invention can also be isolated by exposing a piece of the skin to a digestive enzyme such as trypsin or collagenase (e.g., the skin can be incubated with approximately 0.05% trypsin at 37° C. for approximately five minutes). The chemical dissociation of cells can supplement the mechanical dissociation described herein.

In another aspect, the invention features isolated cells that are non-terminally differentiated progeny of spore-like cells (e.g., an isolated skin progenitor cell descended from a spore-like cell). Skin progenitor cells can be isolated from a variety of sources, including the skin of a post-natal animal and cultures containing spore-like cells. Spore-like cells and their progeny (also referred to herein as skin progenitor cells) are non-terminally differentiated so long as they fail to express a component of keratin, tyrosinase, glutamic acid, glutamate, citrulline, trichohyaline, filagrin, epinephrine, norepinephrine, acetylcholine, or melanin granules.

Spore-like cells and their progeny can be used in many ways. For example, they can be used in conjunction with a skin construct (i.e., with material or devices used to reengineer damaged, diseased, or otherwise unhealthy skin). These constructs can include support structures, such as a mesh, and a hydrogel. Together, the hydrogel and the spore-like cells of the invention form a hydrogel-pore-like cell composition. Similarly, a hydrogel combined with a skin progenitor cell forms a hydrogel-skin progenitor cell composition.

In another aspect, the invention features a method for generating an artificial piece of skin by, for example, combining hydrogel with a spore-like cell or the progeny of a spore-like cell. The hydrogel-cell compositions can be delivered into a permeable, biocompatible support structure. The hydrogel-cell compositions can be used to treat damaged skin (e.g., a hydrogel-spore-like cell composition can be applied to damaged skin).

Also encompassed are spore-like cells or skin progenitor cell isolated by the methods described herein.

Spore-like cells and their progeny must be isolated from their natural environment (i.e., removed from a place where they reside within an animal) to fall within the invention. Accordingly, an "isolated" spore-like cell can be one that is placed in cell culture, even temporarily. The term covers single, isolated spore-like cells and their progeny, as well as cultures of spore-like cells (or their progeny) that have been significantly enriched (i.e., cultures in which less than about 10% of the cells are fully differentiated cells).

As used herein, the terms "progenitor(s)," "neuroectodermal progenitor cell(s)," and "skin progenitor cell(s)" refer to the descendants of spore-like cells that form new skin according to the invention. Spore-like cells and their progeny, which include next generation spore-like cells as well as skin progenitor cells, are non-terminally differentiated cells that can assume or give rise to cells that can assume, the essential phenotype of a number of different cell types (e.g., epithelial cells, keratinocytes, melanocytes, or other cells that form specialized structures (i.e., adnexal structures such as hair follicles and sebaceous glands) within the skin). A cell falls within the invention when it is an undifferentiated cell having the characteristics of a spore-like cell (described herein) or a partially differentiated descendent of a spore-like cell, such as a skin progenitor cell. These undifferentiated spore-like cells and their progeny may or may not be committed to a particular differentiation pathway.

A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions, cross-linking, or similar means. Preferably, the hydrogels used in conjunction with spore-like cells and their progeny solidify so rapidly that the majority of the cells are retained at the application site. This retention enhances new cell growth at the application site. The hydrogels are also biocompatible (e.g., they are not toxic to cells). The "hydrogel-cell composition" referred to herein is a suspension that includes a hydrogel and a spore-like cell or its progeny.

The invention has many advantages. For example, the compositions and methods of the invention can be used to generate skin that is pigmented and that contains adnexal structures (i.e., accessory structures or appendages such as hair follicles, sweat glands, sebaceous glands, nail beds, and specialized sensory receptors that allow us to sense pain, pressure, temperature, position, etc). The pigment and adnexal structures render the skin replacement a more functional and visually appealing replacement (skin equivalent or skin construct) that, optimally, has the appearance of natural, undamaged skin.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The present invention provides compositions and methods for growing new skin, which can be used to repair or replace skin that has been damaged, deformed, or removed by a variety of insults. For example, the compositions and methods of the invention can be used to treat a patient who has suffered a burn (caused, e.g., by exposure to thermal energy such as fire or radiation), any other traumatic injury that damages the skin, a fungal infection that adversely affects the nail beds, ulceration (as occurs, e.g., on the appendages of diabetics or on the pressure bearing areas of paralyzed or bed-ridden patients), a disfiguring disease (e.g., neurofibromatosis), or any disease or condition for which extensive surgery or tissue remodelling is required.

Generally, the methods are carried out by administering spore-like cells or their progeny that have been isolated from a post-natal animal to a damaged area of skin. The spore-like cells can be isolated from the animals' skin or from various other tissues, organs, or bodily fluids (e.g., blood, cerebrospinal fluid, saliva, or urine). These cells can also be administered in numerous contexts (i.e., they can be administered by way of many existing skin replacement or repair protocols). Spore-like cells, their progeny, and methods of administering the cells to a patient are described below.

Spore-like Cells

Spore-like cells and their progeny can be obtained from a donor (e.g., a member of an avian, reptilian, amphibian, or mammalian class). For example, mammalian spore-like cells and their progeny can be isolated from a rodent, a rabbit, a cow, a pig, a horse, a goat, a sheep, a dog, a cat, a non-human primate, or, preferably, a human. Spore-like cells can be obtained from an animal even after it has reached adulthood. Because spore-like cells tolerate oxygen deprivation better than differentiated cells, viable spore-like cells can also be isolated from deceased animals, including animals that have been deceased for many hours (e.g., for at least 4, 6, 12, or even 24 hours or more).

Spore-like cells and their progeny can be obtained from the patient who will be subsequently treated with those cells, from another person, or from an animal of a different species. In other words, autologous, allogeneic, and xenogeneic cells can be obtained and used to treat human or other animal patients.

Regardless of the source from which they are obtained, spore-like cells and their progeny can be placed in culture, and cell lines derived from these cell types can be developed using techniques routinely practiced by those of ordinary skill in the art. Thus, cultured spore-like cells, skin progenitors descended therefrom, and cell lines derived from these cells can all be used to treat human or other animal patients.

Spore-like cells were so-named because of their primitive appearance and tolerance for oxygen deprivation. Spore-like cells are typically small. Many cells in a culture of newly isolated spore-like cells are approximately 1 to 3μ in diameter and, generally, are approximately 1μ in diameter. However, spore-like cells may be larger or smaller than those observed in this seemingly typical range. Given that spore-like cells and skin progenitor cells can differentiate into a variety of mature cell types, and that differentiation is a gradual process, it is difficult to define the precise upper size limit of these cells. However, spore-like cells 4 to 5 and 7 to 10μ in diameter have been identified in electron micrographs, and even larger spore-like cells are believed to exist. The larger cells may be on the verge of cell division or may be conglomerates of several spore-like cells. The lower size limit of the spore-like cells is more definite and is certainly unique. Spore-like cells can be only about one-third of a micron in diameter and some cells may be as small as one-tenth of a micron. This extremely small size may reflect the unique composition of spore-like cells.

Newly isolated spore-like cells are generally spherical and contain a great deal of nuclear material relative to the amount of cytoplasm. The nuclear material appears to be surrounded by a coat containing glycolipids and mucopolysaccharides. Without limiting the invention to spore-like cells that arise by any particular mechanism, it is believed that spore-like cells may arise when essential DNA fragments are shed from mature cells (e.g., those undergoing cell death by apoptosis or other means) and repackaged in a primitive coating of glycolipids and mucopolysaccharides.

Functionally, spore-like cells are unique in at least three ways. First, even though isolated from a mature (e.g., a postnatal, adolescent, or adult) animal, they can differentiate into a wide variety of different cell types. Second, spore-like cells have an exceptionally high tolerance for oxygen deprivation. Viable spore-like cells have been isolated from adult mammals that have been deceased for either approximately 4 or 24 hours. Thus, spore-like cells can tolerate essentially complete oxygen deprivation for at least 24 hours. In addition, spore-like cells have a greater capacity to proliferate than terminally differentiated cells isolated from specialized tissues. Proliferative capacity is an important attribute because tissue engineering, cell therapies, and gene-based therapies are often hampered by physicians' inability to obtain sufficient numbers of cells to administer to a patient.

As described herein, spore-like cells and skin progenitor cells can be isolated from larger, more differentiated cells by a procedure that includes trituration with a pipette having a reduced bore. However, one of ordinary skill in the art will recognize that trituration is not the only way to isolate spore-like cells and skin progenitor cells from larger, more differentiated cells. For example, a suspension containing spore-like cells, skin progenitor cells, and fully differentiated cells can be passed through a filter having pores of a particular size. The size of the pores within the filter (and, similarly, the diameter of the pipette used for trituration) can be varied, depending on how stringent one wishes the isolation procedure to be. Generally, the smaller the pores within the filter, or the smaller the diameter of the pipette used for trituration, the fewer the number of differentiated cells that will survive the isolation procedure. Without limiting the invention to spore-like cells or skin progenitor cells that differentiate by a particular mechanism, it is believed that the rate and direction of differentiation (i.e., the fate of spore-like cells and skin progenitor cells) can be influenced by altering the number and type of differentiated cells to which the spore-like cells are exposed. For example, the more differentiated skin cells that remain in a culture of spore-like cells or skin progenitor cells, the more quickly these undifferentiated cells will differentiate and the more likely it is that they will differentiate into a type of skin cell.

At the time of isolation, spore-like cells may not express any known markers (i.e., proteins or other biological molecules associated with a given terminally differentiated cell type). When placed in culture, some spore-like cells can express nestin, a marker of neuroectodermally-derived cells. While a quantitative study has not yet been performed, it appears that the nestin-positive cells are among the larger cells in culture. Spore-like cells or skin progenitor cells will eventually express cellular markers associated with terminally differentiated skin cells (see the Examples below). Those of ordinary skill in the art can identify, by techniques routinely practiced in the art (e.g., immunochemistry), numerous markers associated with terminally differentiated skin cells. Those of ordinary skill in the art can also readily compare the cytoarchitecture of spore-like cells, their progeny, and known terminally differentiated cells in order to distinguish one from another. This comparison can be made, for example, using electron microscopy.

The features and characteristics described herein can be used to distinguish spore-like cells and skin progenitor cells from previously identified cell types. For example, spore-like cells can be identified by their ability to differentiate into a variety of terminally differentiated cell types found in mature skin, their typical spherical shape, their small size (as small as 0.1-0.3μ in diameter), and their cytoarchitecture (which includes relatively large amounts of nuclear material, relatively small amounts of cytoplasm, and a coat rich in glycolipids and mucopolysaccharides), and their ability to survive in environments having a low or even non-existent oxygen supply.

When cultured as described in the Examples below, spore-like cells proliferate more rapidly and into more types of differentiated cells than do terminally differentiated cells or mesenchymal stem cells. Cell viability can be assessed using standard techniques, including visual observation with light or scanning electron microscopes and Trypan blue exclusion.

Spore-like cells and skin progenitor cells can proliferate and differentiate in response to agents (e.g., growth factors or hormones) within tissue, including tissue that has been injured or that is otherwise associated with a medical disorder. These agents guide differentiation so that the spore-like cells or their progeny come to express the phenotype of mature cells normally present in the tissue in which they have been placed.

Spore-like cells and their progeny can be induced to differentiate in a variety of ways and may or may not be committed to a particular differentiation pathway. The compositions of the invention are not limited to cells that differentiate by any particular mechanism.

One method of inducing differentiation is to allow spore-like cells or their progeny to establish contact (e.g., physical contact) with a solid support. For example, spore-like cells can differentiate when they establish contact with a glass or plastic surface, a mesh, or other substrate suitable for use in tissue culture or administration to a patient. Contact can be facilitated by coating the solid support with one or more components of the extracellular matrix, such as laminin or fibronectin. On the other hand, keeping the cells suspended tends to inhibit differentiation.

Spore-like cells can also differentiate when they establish contact with a tissue within a patient's body or when they are sufficiently close to a tissue to be influenced by substances (e.g., growth factors, enzymes, or hormones) released from the tissue. In other words, a spore-like cell can establish contact with a tissue (e.g., the dermis or epidermis) by virtue of receiving signals from the tissue. Such signalling would occur, for example, when a receptor on the surface of a spore-like cell, or on the surface of a cell descended from a spore-like cell (e.g., a skin progenitor cell), binds and transduces a signal from a molecule such as a growth factor, enzyme, or hormone that was released by a tissue within the patient.

Alternatively, or in addition, spore-like cells and skin progenitor cells can be induced to differentiate by adding a substance (e.g., a growth factor, enzyme, hormone, or other signalling molecule) to the cell's environment. For example, a substance can be added to a culture dish containing spore-like cells, to a mesh or other substrate suitable for applying spore-like cells to a tissue, or to a tissue within a patient's body. When a substance that induces spore-like cells to differentiate is administered, either systemically or locally, it can be administered according to pharmaceutically accepted methods. For example, proteins, polypeptides, or oligonucleotides can be administered in a physiologically compatible buffer, with or without a carrier or excipient. Of course, either the cells within a patient's body or the cells being administered (here, spore-like cells or their progeny) can be made to express particular factors following genetic manipulation. Thus, spore-like cells or their progeny can differentiate either in culture or in a patient's body, and may do so following contact with a solid support or exposure to substances that are either naturally expressed, exogenously administered, or expressed as a result of genetic manipulation. Regardless of the stimulus for differentiation, spore-like cells or skin progenitor cells that will differentiate or have differentiated sufficiently to aid in the maintenance or repair of the dermis or epidermis, can be administered to a patient (e.g., at the site of a burn or other traumatized area of skin).

While spore-like cells or their progeny may eventually become fully differentiated, and while this is desirable in some circumstances (e.g., where the cells are used to recreate a histologically mature and complete tissue), not all of the cells administered need to be fully differentiated to achieve successful treatment; spore-like cells or skin progenitor cells need only differentiate to a point sufficient to treat the patient. That point may be reached either before or after the cells are administered to the patient.

As described herein, spore-like cells and skin progenitor cells can be isolated from a variety of sources. More specifically, the cells can be obtained from an excisional biopsy. For example, the skin can be swabbed with betadine and infiltrated with lidocaine. Under sterile conditions, a piece of skin can then be removed with a scalpel or punch. Once obtained, the dermis, the epidermis, or full-thickness skin can be placed in culture. If desired, spore-like cells or skin progenitor cells can be isolated individually from both the dermis and epidermis.

To obtain spore-like cells or skin progenitor cells, the piece of skin is placed in a buffered solution (e.g., phosphate buffered saline), which can include one or more antibiotics, and the tissue can be dissociated mechanically (e.g., by macerating the tissue or by scraping it with a scalpel or similar instrument), chemically (e.g., by exposure to one or more enzymes, such as trypsin or collagenase, that facilitate tissue degradation), or both. Generally, the more aggressive the dissociation, the more spore-like cells or skin progenitor cells one will obtain. To isolate individual spore-like cells or skin progenitor cells, the tissue can be triturated, first with a normal bore Pasteur pipette and subsequently with a series of fire polished pipettes having bore sizes ultimately reduced to less than about fifteen microns. This procedure (which is described in further detail in the Examples below) destroys large mature cells, but allows the smaller spore-like cells and skin progenitor cells (i.e., cells having a diameter smaller than that of the smallest bore pipette) to survive.

The surviving cells are placed in an incubator and can be grown under conditions that either allow them to proliferate and differentiate into the specialized cell types found in mature skin or that discourage differentiation. For example, spore-like cells and skin progenitor cells can be encouraged to differentiate by exposing them to the processes and basal nutrient media described in U.S. Pat. No. 5,292,655. Alternatively, growth factors that cause progenitor cells to mitose (e.g., epidermal growth factor (EGF), basic fibroblast growth factor (bFGF) and other cytokines) can be applied to help maintain the cells in an undifferentiated state. For example, the isolated cells can be cultured in Dulbecco's Modified Eagle's Medium (DMEM) supplemented with a hormone mixture containing glucose, transferrin, insulin, putricine, selenium, progesterone, EGF, and bFGF. The cells can be incubated in, for example, 75 $cm^2$ tissue culture flasks, at 37° C. in 5% $CO_2$. The media can be changed approximately every three days, and cells can be passaged approximately every 7-9 days. More specifically, spore-like cells and skin progenitor cells can be isolated and cultured as described in the Examples below.

Another way to promote proliferation without differentiation is to expose skin progenitor cells to agonists of Notch function, as described in U.S. Pat. No. 5,780,300. Agonists of Notch include, but are not limited to, proteins such as Delta or Serrate or Jagged (Lindsell et al., *Cell* 80:909-917, 1995) or biologically active fragments thereof. These proteins or protein fragments mediate binding to Notch and thereby activate the Notch pathway. Spore-like cells or skin progenitor cells can be contacted in culture with agonists of Notch or can be transfected with genes that encode Notch agonists. The techniques required to transfect cells in culture are routinely practiced by those of ordinary skill in the art. Progenitors that remain undifferentiated in culture can differentiate when administered to a patient; their differentiation being orchestrated by the microenvironment they encounter within the patient.

Cells obtained from an immunologically distinct donor may illicit an immune response, in which case, the patient (the recipient of the cells) can be treated with standard immunosuppressant therapy (e.g., with cyclosporine and/or steroid hormones). While immunosuppression is commonly required when transplanting typical mature cells (e.g., when transplanting an organ such as the liver or kidney), it may not be required when administering the unique cells of the invention. These cells, particularly spore-like cells, are so undifferentiated that they may not express surface antigens and thus would not elicit an immune response, even if isolated from a different species or a different individual of the same species as the patient who will receive the cells.

When cultured under the conditions described in the Examples below, skin progenitor cells appear to double approximately every 24-36 hours. Cell viability can be assessed using standard techniques, including visual observation with a light or scanning electron microscope and Trypan blue exclusion.

While it is difficult to definitively demonstrate, studies to date suggest that skin progenitor cells isolated from the epidermis give rise to epidermal cells (e.g., melanocytes, keratinocytes, and Merkel cells) and progenitor cells isolated from the dermis give rise to dermal cells (e.g., the cells that make up sweat glands, sebaceous glands, and hair follicles). Whether these lineages are exclusive (i.e., whether progenitors isolated from the epidermis and dermis can give rise only to epidermal and dermal cell types, respectively) remains to be seen. Spore-like cells from either tissue will likely give rise to all, or most, types of skin cells.

Terminal differentiation occurs when a skin progenitor cell expresses essentially the same phenotype as a mature skin cell. For example, for the purpose of defining this invention, a skin progenitor cell is differentiated when it expresses one or more of the proteins expressed by a mature keratinocyte (which include components of keratin, the most prominent of which are K-1, K-10, K-15, and K-14); or by a mature melanocyte (which expresses, e.g., tyrosinase); by a mature hair follicle (which expresses, e.g., glutamic acid, glutamate, citrulline, tricohyaline (hard keratin) and filagrin (soft keratin); or by a mature neuron (which expresses epinephrine or norepinephrine as a sympathetic neuron or acetylcholine as a parasympathetic neuron). The markers listed herein can be identified by either standard immunocytochemistry or biochemistry. In addition, histological stains and microscopy can be used to identify mature skin cells. For example, electron microscopy can be performed to reveal melanosomes, and a Fontana stain can be performed to identify melanin granules in melanocytes. Electron microscopy is also useful in identifying dense core granules in another epithelial cell type, the Merkel cell. Analysis of cellular morphology can also be used to identify sweat glands, which contain clear cells filled with glycogen, and sebaceous glands that are filled with lipids, triglycerides, cholesterol, and wax-like substances.

Methods of Treatment

A. Administration of Spore-like Cells and Skin Progenitor Cells via Hydrogel

The novel cell types described herein can be administered to a patient by way of a composition that includes spore-like cells and/or skin progenitor cells or their progeny and a liquid hydrogel. This cell-hydrogel mixture can be applied directly to an area of the skin that has been damaged. For example, as described in U.S. Ser. No. 08/747,036, a hydrogel-cell mixture can be easily applied, essentially being brushed, dripped, or sprayed, onto a desired surface. The hydrogel provides a thin matrix or scaffold within which the skin progenitor cells adhere and grow. This method of administration may be especially well suited when the damaged area of skin has an irregular shape. Preferably, progenitor cells isolated from the dermal layer of the skin are applied first and progenitor cells isolated from the epidermal layer of the skin are applied second (i.e., progenitors isolated from the epidermis are on top of those isolated from the dermis).

Alternatively, the hydrogel-cell mixture can be introduced into a permeable, biocompatible support structure so that the mixture essentially fills the support structure and, as it solidifies, assumes the support structure's shape. Thus, the support structure can guide the development and shape of the tissue that matures from skin progenitor cells placed within it. As described further below, the support structure can be provided to a patient either before or after it has been filled with the hydrogel-cell mixture. For example, the support structure can be placed within a damaged area of the skin and subsequently filled with the hydrogel-cell composition using a syringe, catheter, or other suitable device. Preferably, the shape of the support structure will conform to, or be made to conform to, the shape of the damaged tissue. In the following subsections, suitable support structures, hydrogels, and delivery methods are described (cells suitable for use are described above).

1. Hydrogels

A variety of hydrogels can be used to practice the present invention. They include, but are not limited to: (1) temperature dependent hydrogels that solidify or set at body temperature, e.g., PLURONICS™; (2) hydrogels cross-linked by ions, e.g., sodium alginate; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™.

The materials that can be used to form these various hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Ionic Hydrogels

Ionic polysaccharides, such as alginates or chitosan, can be used to suspend living cells. In one example, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

Skin progenitor cells are mixed with an alginate solution, the solution is delivered to an already implanted support structure and then solidifies in a short time due to the presence in vivo of physiological concentrations of calcium ions. Alternatively, the solution is delivered to the support structure prior to implantation and solidified in an external solution containing calcium ions. In addition, the support structure itself can be coated with or contain the appropriate ions, for example, calcium cations, to cause an ionic hydrogel to solidify once introduced into the support structure.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorus atoms separated by alternating single and double bonds. Each phosphorus atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Polyphosphazenes that erode in vivo have at least two different types of side chains: acidic side groups capable of forming salt bridges with multivalent cations, and side groups that hydrolyze under in vivo conditions, e.g., imidazole groups, amino acid esters, glycerol, and glucosyl. Degradable polymers, i.e., polymers that dissolve or degrade within a period that is acceptable in the desired application (usually in vivo therapy), will degrade in less than about five years and most preferably in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described herein are known to those of ordinary skill in the art. See, for example *Concise Encyclopedia of Polymer Science and Engineering*, J. I. Kroschwitz, editor (John Wiley and Sons, New York, N.Y., 1990). Many polymers, such as poly(acrylic acid), alginates, and PLURONICS™, are commercially available. Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10 kDa and 18.5 kDa. Smaller polymers result in gels of higher density with smaller pores.

Temperature-Dependent Hydrogels

Temperature-dependent, or thermosensitive, hydrogels can be use in the methods of the invention. These hydrogels have so-called "reverse gelation" properties, i.e., they are liquids at or below room temperature, and gel when warmed to higher temperatures, e.g., body temperature. Thus, these hydrogels can be easily applied at or below room temperature as a liquid and automatically form a semi-solid gel when warmed to body temperature. As a result, these gels are especially useful when the support structure is first implanted in or applied to a patient, and then filled with the hydrogel-cell composition, or when they are painted on a patient without the use of a support structure. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to alter physical properties such as their porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing cells to survive and be nourished.

U.S. Pat. No. 4,188,373 describes the use of PLURONIC™ polyols in aqueous compositions to provide thermal gelling aqueous systems. U.S. Pat. Nos. 4,474,751, '752, '753, and 4,478,822 describe drug delivery systems that utilize thermosetting polyoxyalkylene gels. With these systems, both the gel transition temperature and/or the rigidity of the gel can be modified by adjusting the pH and/or the ionic strength, as well as by the concentration of the polymer.

pH-Dependent Hydrogels

Other hydrogels suitable for use in the methods of the invention are pH-dependent. These hydrogels are liquids at, below, or above specific pH values, and gel when exposed to specific pH values, e.g., 7.35 to 7.45, which is the normal pH range of extracellular fluids within the human body. Thus, these hydrogels can be easily delivered to a support structure as a liquid and automatically form a semisolid gel when exposed to body pH. Examples of such pH-dependent hydrogels are TETRONICS™ (BASF-Wyandotte) polyoxyethylene-polyoxypropylene polymers of ethylene diamine, poly (diethyl aminoethyl methacrylate-g-ethylene glycol), and poly(2-hydroxymethyl methacrylate). These copolymers can be manipulated by standard techniques to affect their physical properties.

Light Solidified Hydrogels

Other hydrogels that can be used in the methods of the invention are solidified by either visible or ultraviolet light. These hydrogels are made of macromers including a water soluble region, a biodegradable region, and at least two polymerizable regions as described in U.S. Pat. No. 5,410,016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity. Light solidified hydrogels are useful, for example, for direct painting of the hydrogel-cell mixture onto damaged tissue.

Regardless of type, a hydrogel used to practice this invention should be biocompatible, biodegradable, and, preferably, able to solidify rapidly in vivo (i.e., in about 5 minutes or so following delivery to the support structure). The hydrogel should also sustain living cells.

2. Preparation of Hydrogel-Cell Mixtures

Once a hydrogel of choice (e.g., a thermosensitive polymer at between 5 and 25% (W/V), or an ionic hydrogel such as alginate dissolved in an aqueous solution (e.g., a 0.1 M potassium phosphate solution, at physiological pH, to a concentration between 0.5% to 2% by weight) is prepared, isolated spore-like or progenitor cells are suspended in the polymer solution. The concentration of the cells can mimic that of the tissue to be generated. For example, the concentration of cells can range between 10 and 100 million cells/ml (e.g., between 20 and 50 million cells/ml). Of course, the optimal concentration of cells to be delivered into the support structure may be determined on a case by case basis, and may vary depending on cell type and the region of the patient's body into which the support structure is implanted or onto which it is applied. To optimize the procedure (i.e., to provide optimal viscosity and cell number), one need only vary the concentrations of the cells or the hydrogel.

3. Support Structures

The support structure is a permeable structure having pore-like cavities or interstices that shape and support the hydrogel-cell mixture. For example, the support structure can be a porous polymer mesh, or a natural or synthetic sponge. The porosity of the support structure should be such that nutrients can diffuse into the structure, thereby effectively reaching the cells inside, and waste products produced by the cells can diffuse out of the structure.

The support structure can be shaped to conform to the space in which new tissue is desired. For example, the support structure can be shaped to conform to the shape of an area of the skin that has been burned. Depending on the material from which it is made, the support structure can be shaped by cutting, molding, casting, or any other method that produces a desired shape (as described herein, in some instances, the support structure can be shaped by hand). Moreover, the shaping process can occur either before or after the support structure is filled with the hydrogel-cell mixture. For example, a support structure can be filled with a hydrogel-cell mixture and, as the hydrogel hardens, molded into a desired shape by hand.

As the hydrogel solidifies, it will adopt the flexibility and resiliency of the support structure, which is important for accommodation of compressive and tensile forces. Thus, for example, replaced skin could accommodate tensile forces associated with pulling and stretching, as well as compressive forces associated with weight bearing, (as occurs, e.g., on the soles of the feet). The flexibility and resiliency of the support structure also provides greater ease of administration. In many currently available skin replacement methods, the tissue is extremely delicate and must be handled with the utmost care.

The support structure is also biocompatible (i.e., it is not toxic to the cells suspended therein) and can be biodegradable. Thus, the support structure can be formed from a synthetic polymer such as a polyanhydride, polyorthoester, or polyglycolic acid. The polymer should provide the support structure with an adequate shape and promote cell growth and proliferation by allowing nutrients to reach the cells by diffusion. Additional factors, such as growth factors, other factors that induce differentiation or dedifferentiation, secretion products, immunomodulators, anti-inflammatory agents, regression factors, biologically active compounds that promote innervation or enhance the lymphatic network, and drugs, can be incorporated into the polymer support structure. An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape.

Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Many other types of support structures are also possible. For example, the support structure can be formed from sponges, foams, corals, or biocompatible inorganic structures having internal pores, or mesh sheets of interwoven polymer fibers. These support structures can be prepared using known methods.

4. Application of the Support Structure

Figure 4:
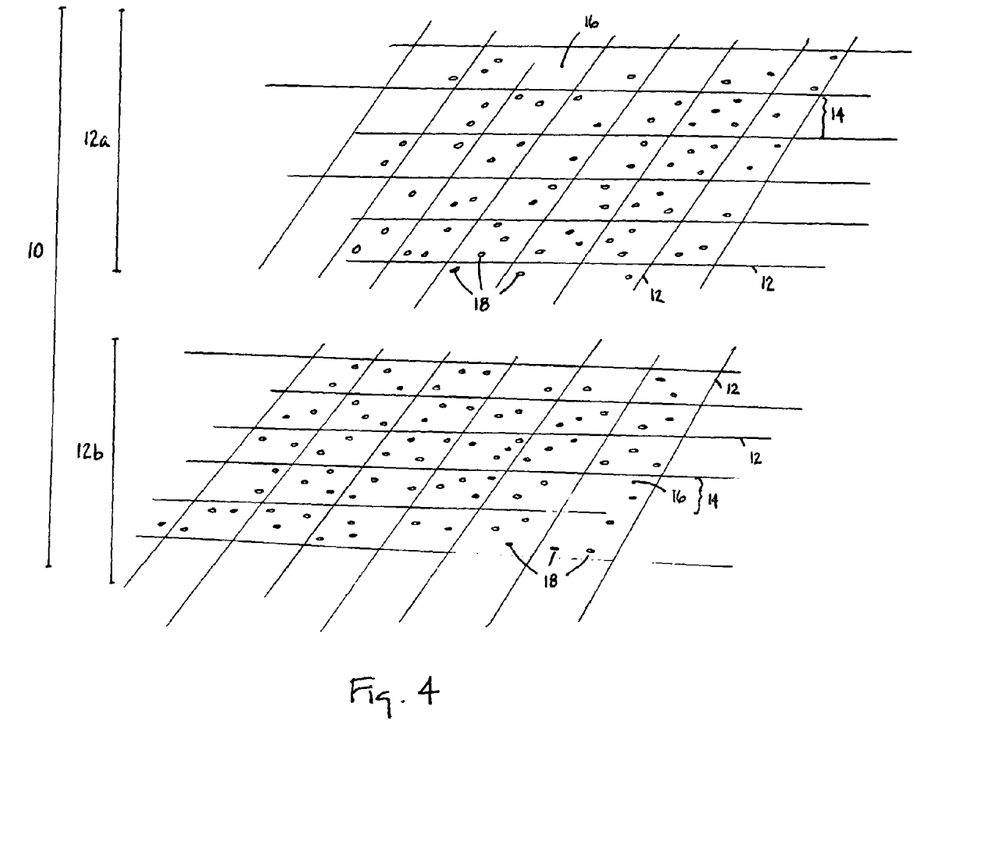
FIG. 4 is a schematic of a permeable support structure filled with a hydrogel-cell composition to form an epidermal layer and a juxtaposed (underlying) dermal layer. The epidermal and dermal layers include sheets of mesh that are identical except for the cells they contain.
Figure 5:
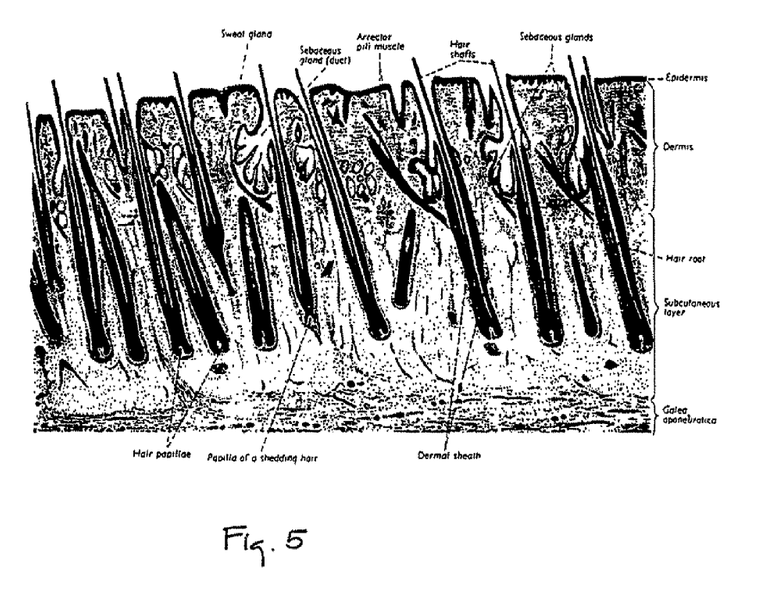
FIG. 5 is a schematic of an optimal skin construct in cross-section. This construct contains many hair follicles and would be suitable for use on the scalp, arm, or leg.

Any of the liquid hydrogel-cell mixtures described above can be placed in any of the permeable support structures (also described above). FIG. 4 is a schematic of a filled support structure in cross-section. The support structure 10 is formed from a bilayered mesh of interwoven polymer fibers 12 having epidermal layer 12a and dermal layer 12b. The spaces between the fibers form interconnected pores 14 that are filled with liquid hydrogel-cell mixture. Within a short time of placing the mixture in the support structure (e.g., in approximately three to five minutes), hydrogel 16 solidifies, thereby keeping the suspended cells 18 within the pores 14 of support structure 10. The solidified hydrogel 16 helps maintain the viability of the cells by allowing diffusion of nutrients (including growth and differentiation factors) and waste products through the interconnected pores of the support structure. The ultimate result being the growth of new skin and its engraftment to the patient's body.

The liquid hydrogel-cell mixture can be delivered to the shaped support structure either before or after the support structure is implanted in or applied to a patient. The specific method of delivery will depend on whether the support structure is sufficiently "sponge-like" for the given viscosity of the hydrogel-cell composition, i.e., whether the support structure easily retains the liquid hydrogel-cell mixture before it solidifies. Sponge-like support structures can be immersed within, and saturated with, the liquid hydrogel-cell mixture, and subsequently removed from the mixture. The hydrogel is then allowed to solidify within the support structure. The hydrogel-cell-containing support structure is then implanted in or otherwise applied to the patient's skin.

The support structure can also be applied to the patient before the hydrogel completely solidifies. Alternatively, a sponge-like support structure can be injected with the liquid hydrogel-cell mixture, either before or after the support structure is implanted in or applied to the patient. The hydrogel-cell mixture is then allowed to solidify.

The volume of the liquid hydrogel-cell mixture injected into the support structure is typically less than, but somewhat comparable to the volume of the support structure, i.e., the volume of the desired tissue to be grown.

Support structures that do not easily retain the liquid composition require somewhat different methods. In those cases, for example, the support structure is immersed within and saturated with the liquid hydrogel-cell mixture, which is then allowed to partially solidify. Once the cell-containing hydrogel has solidified to the point where the support structure can retain the hydrogel, the support structure is removed from the partially solidified hydrogen, and, if necessary, partially solidified hydrogel that remains attached to the outside of the support structure is removed, e.g., scraped off the structure.

Alternatively, the liquid hydrogel-cell mixture can be delivered into a mold containing the support structure. For example, the liquid hydrogel-cell mixture can be injected into an otherwise fluid-tight mold that contains the support structure and matches its outer shape and size. The hydrogel is then solidified within the mold, for example, by heating, cooling, light-exposure, or pH adjustment, after which, the hydrogel-cell-containing support structure can be removed from the mold in a form that is ready for implantation.

In other embodiments, the support structure is implanted in or applied to the patient (e.g., placed over the site of a burn or other wound), and the liquid hydrogel-cell mixture is then delivered to the support structure. The hydrogel-cell mixture can be delivered to the support using any simple device, such as a syringe or catheter, or merely by pouring or "painting" a liquid gel onto a sheet-like support structure.

Here again, the volume of hydrogel-cell composition added to the support structure should approximate the size of the support structure (i.e., the volume displaced by the desired tissue to be grown). The support structure provides space and a structural template for the injected liquid hydrogel-cell mixture. As described herein, some of the hydrogel-cell mixture may leak from the support structure prior to solidifying. However, in this event, existing tissue (e.g., underlying dermis, muscle, bone, or cartilage) beneath the support structure would sufficiently constrain the liquid hydrogel-cell mixture until it gels.

In any of the above cases, the hydrogel is solidified using a method that corresponds to the particular hydrogel used (e.g., gently heating a composition including a PLURONIC™ temperature-sensitive hydrogel).

To apply or implant the support structure, the implantation site within the mammalian patient can be prepared (e.g., by debridement), and the support structure can be implanted or otherwise applied directly at that site. If necessary, during implantation, the site can be cleared of bodily fluids such as blood (e.g., with a burst of air or suction).

B. Administration of Spore-like and Skin Progenitor Cells in Connection with Existing Skin Replacement Therapies Spore-like cells and/or skin progenitor cells can also be administered in connection with existing skin replacement therapies. Including these cells improves existing methods in that the cells, by differentiating into cell types and structures that would not otherwise be present, improve the structure, functions, and appearance of the replacement skin.

1. Use of Spore-like Cells or Skin Progenitor Cells with Dermagraft™

Spore-like cells and/or skin progenitor cells can be administered in connection with dermal tissue replacements that are placed beneath meshed, split-thickness skin grafts. To construct the tissue replacement, human dermal fibroblasts are isolated from neonatal foreskin as follows. Epidermis and dermis are separated by incubation in 0.25% trypsin with 0.2% ethylenediaminetetraacetic acid for 1-2 hours at 37° C. The dermis is minced and digested with collagenase B, and the tissue digest is filtered through sterile gauze to remove debris. Fibroblasts are maintained in Dulbecco's modified eagle's medium (DMEM) and passaged when cells reach 80-90% confluence. Cells are removed from flasks and resuspended for seeding at a concentration of $4 \times 10^6$ cells/ml. Concurrently, skin progenitor cells are isolated and cultured as described herein, and resuspended for seeding at a concentration of approximately $4 \times 10^6$ cells/ml.

Dermal grafts are then prepared by seeding viable fibroblasts and skin progenitor cells in a minimum volume of DMEM onto each 4 cm$^2$ area by Vicryl™ mesh (Ethicon Inc., Somerville, N.J.). The cells readily attach in vitro to the mesh fibers, and they become confluent in 2 to 3 weeks (i.e., all mesh openings are covered by cells and tissue matrix, according to assay by inverted phase microscopy).

The wound site can be excised to subcutaneous fat, to fascia, or to deep dermis and fat. Hemostatis can be achieved with topical thrombin-epinephrine solution and electrocoagulation. The graft, prepared as described above, is placed on the prepared site and affixed to the wound margins with staples or sutures. If desired, a hydrogel can be used together with the Vicryl™ mesh.

2. Use of Spore-like Cells and Skin Progenitor Cells with Collagen-Based Skin Substitutes Spore-like cells and/or skin progenitor cells can be used in conjunction with numerous permanent dermal skin replacements that include, for example, resorbable synthetic composites containing collagen and chondroitin-6-sulfate (e.g., glycosaminoglycan (GAG) dermal membranes are described by Burke et al., *Ann. Surg.* 194:413-428, 1981; Yannas et al., *Science* 214:174-176, 1982; and Yannas et al., U.S. Pat. No. 4,060,081). Spore-like cells and skin progenitor cells can also be used in lieu of keratinocytes in the dermal collagen-chondroitin-6-sulfate membrane described in EP 0 363 400 B1 or in the collagen matrices that include transforming growth factor-$\beta$ (TGF-$\beta$) described in U.S. Pat. No. 5,800,811. TGF-$\beta$ impregnated collagen matrices may be advantageous in that they are thought to inhibit inflammatory processes while promoting angiogenesis and histogenesis.

3. Use of Spore-like Cells and Progenitor Cells with Multilayer Skin Substitutes Spore-like cells and skin progenitor cells are especially well suited for use with multilayer skin substitutes. Spore-like cells or progenitor cells isolated from the dermis can be incorporated in the lower or "dermal" layer, where they would subsequently differentiate into adnexal structures, and spore-like cells or progenitor cells isolated from the epidermis can be incorporated in the upper or "epidermal" layer, where they would subsequently differentiate into melanocytes cells, keratinocytes, and Merkel cells. Several multilayer skin equivalents that can be used in conjunction with skin progenitor cells are described in WO 97/41208.

C. In Vivo Testing

Numerous in vivo models of wound healing are available in which to test spore-like cells and skin progenitor cells isolated by the methods described herein. For example, the ability of these cells to repair a burn can be tested in domestic outbred swine. The swine are anaesthesized by ketamine hydrochloride, followed by inhalation of a mixture of halothane, nitrous oxide, and oxygen. A portion of their skin is shaved, washed twice with Betadine™, and washed once with 70% alcohol. Wounds that are 1 mm deep are then created with a Brown dermatome on the lateral side. Wounds of this depth correspond to deep second degree burns and remove all of the epidermis and most of the dermis. Of course, the depth of the injury can be increased to mimic a more severe burn or decreased to mimic a less severe burn. The size of the wounds can also be varied. Typically, a wound is approximately 2.5 inches square. Following surgery, the pigs are treated with analgesics to alleviate pain.

A second reliable skin injury model has been developed in pigs to study the use of hyaluronidase in the treatment of intravenous extravasation injuries (Raszka et al., *J. Perinatol.* 10:146-149, 1990). In this model, the flanks of recently weaned Yorkshire pigs are shaved and then cleaned with alcohol and povidone-iodine solutions. A subcutaneous injection of $CaCl_2$ (300 mEq/L; 2.0 ml) is then given, which causes ulceration (an area of full thickness skin necrosis greater than 0.5 $cm^2$)

Murine wound healing models are also available. For example, Moore et al. (*Br. J. Cancer* 66:1037-1043, 1992) describe a model that can be used to compare patterns of damage to skin and its supporting vasculature following treatment by hyperthermia and photodynamic therapy. More straight-forward injury models are also available. For example, rodents used in studies of hyperthermia have received burns by exposure to a heat source. For example, an area of the skin can be injured by exposure to hot water (98° C.) for a given number of seconds (9 seconds; as in Farriol et al., *Burns* 20:496-498, 1994).

EXAMPLES

The present invention will be further understood by reference to the following non-limiting examples.

Example 1

Isolation of Skin Progenitor Cells from an Adult Fisher Rat

Excisional biopsies of the skin of adult Fisher rats were made under sterile conditions. The biopsied tissue, which included the dermis and epidermis, was placed in a petri dish containing cold (50° C.) phosphate buffered saline (PBS) and antibiotics (penicillin (50 mU/ml) and streptomycin (90 mg/ml)). The epidermis was scraped with a #11 scalpel to disassociate epidermal cells, and the tissue was then transferred to a second petri dish (also containing cold PBS and antibiotic) where the dermis was scraped with a #11 scalpel. The cells that were dissociated were then centrifuged at 1200 rpm (GLC-2B, Sorvall, Wilmington, Del.) for five minutes and resuspended in 10 ml of 0.05% trypsin (Life Technologies, Baltimore, Md.). Following resuspension in trypsin, the tissue was incubated at 37° C. for five minutes. Ten ml of Dulbecco's Modified Eagle Medium (DMEM)/F-12 containing 10% heat inactivated fetal bovine serum (FBS) (Life Technologies, Baltimore, Md.) was added to deactivate the trypsin.

The tissue was then triturated, first with a normal bore Pasteur pipette and subsequently with a series of fire polished pipettes having bores reduced to about 15 µm. The number of pipettes required can vary depending upon how frequently they become clogged with tissue. Trituration was carried out until the tissue was dispersed as a fine suspension. The suspension was then centrifuged at 1200 rpm (GLC-2B, Sorvall, Wilmington, Del.) for five minutes. The supernatant was removed and the pellet was resuspended in 15 ml of DMEM/F-12 medium supplemented with a hormone mixture containing glucose (23 mM), transferrin (10 mg/ml), insulin (20 mg/ml), putricine (10 mM), selenium (100 nM), progesterone (10 nM) (Life Technologies, Baltimore, Md.), EGF (20 ng/ml) and bFGF (20 ng/ml) (Collaborative Biomedical Products, Chicago, Ill.). The suspension was transferred to 75 $cm^2$ tissue culture flasks (Collaborative Biomedical Products, Chicago, Ill.) and incubated at 37° C. in 5% $CO_2$. The media was changed every three days and cells were passaged every 7-9 days. The cells that attached to the tissue culture flask seemed more prone to differentiate.

Example 2

Isolation of Skin Progenitor Cells from an Adult Pig

Excisional biopsies of the skin of adult pigs were made under sterile conditions. The biopsied tissue, which included the dermis and epidermis, was placed in a petri dish containing cold (50° C.) phosphate buffered saline (PBS) and antibiotics (penicillin (50 mU/ml) and streptomycin (90 mg/ml)). The epidermis was scraped with a #11 scalpel to disassociate epidermal cells, and the tissue was then transferred to a second petri dish (also containing cold PBS and antibiotic) where the dermis was scraped with a #11 scalpel. The dissociated cells were then centrifuged at 1200 rpm (GLC-2B, Sorvall, Wilmington, Del.) for five minutes and resuspended in 10 ml of 0.05% trypsin (Life Technologies, Baltimore, Md.). Following resuspension in trypsin, the tissue was incubated at 37° C. for five minutes. Ten ml of Dulbecco's Modified Eagle Medium (DMEM)/F-12 containing 10% heat inactivated fetal bovine serum (FBS) (Life Technologies, Baltimore, Md.) was added to deactivate the trypsin. The tissue was then triturated, first with a normal bore Pasteur pipette and subsequently with a series of fire polished pipettes having reduced bores. Trituration was carried out until the tissue was dispersed as a fine suspension.

The suspension was then centrifuged at 1200 rpm (GLC-2B, Sorvall, Wilmington, Del.) for five minutes. The supernatant was removed and the pellet was resuspended in 15 ml of DMEM/F-12 medium supplemented with a hormone mixture containing glucose (23 mM), transferrin (10 mg/ml), insulin (20 mg/ml), putricine (10 mM), selenium (100 nM), progesterone (10 nM) (Life Technologies, Baltimore, Md.), EGF (20 ng/ml) and β-FGF (20 ng/ml) (Collaborative Biomedical Products, Chicago, Ill.). The suspension was transferred to 75 $cm^2$ tissue culture flasks (Collaborative Biomedical Products, Chicago, Ill.) and incubated at 37° C. in 5% $CO_2$. The media was changed every three days and cells were passaged every 7-9 days.

Example 3

Differentiation of Progenitor Cells Isolated From an Adult Fisher Rat

Figure 1:
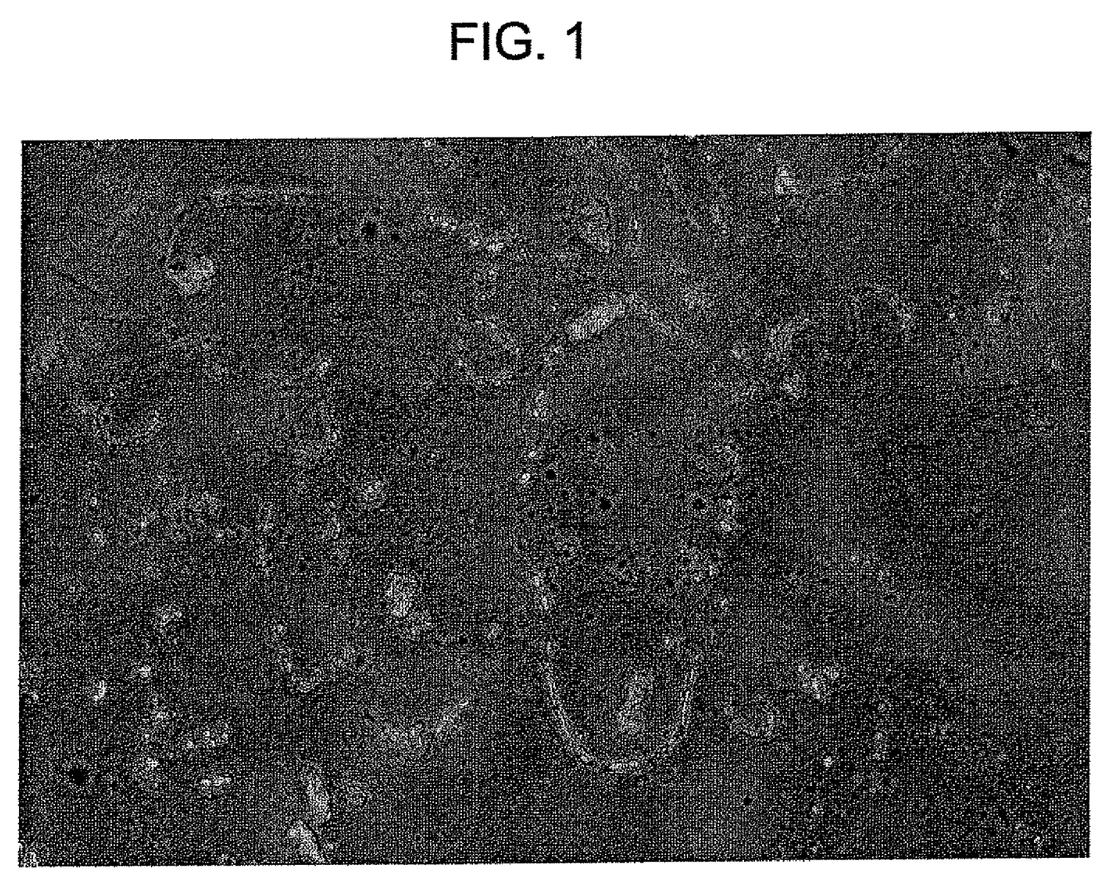
FIG. 1 is a photograph of skin progenitor cells following partial differentiation into an unidentified adnexal skin structure (magnification is 200×).
Figure 2:
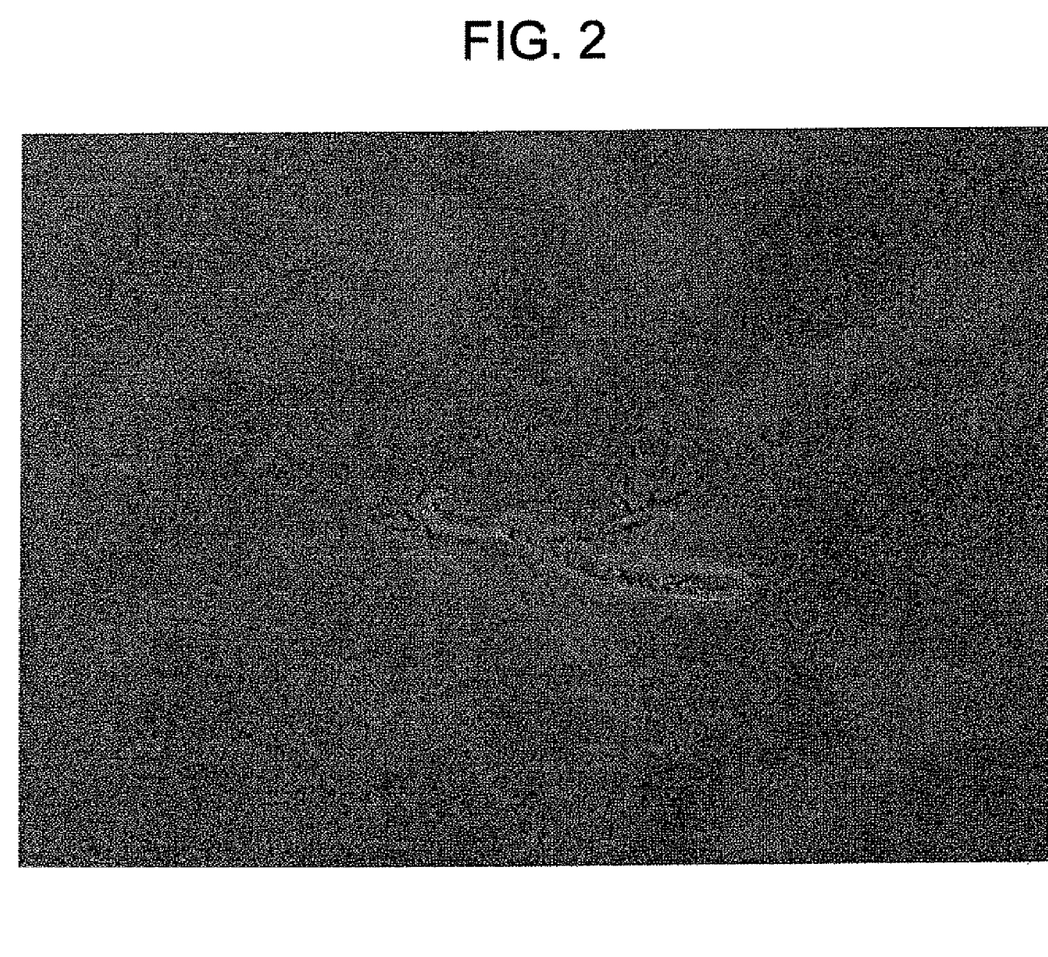
FIG. 2 is a photograph of a primitive adnexal gland. The photograph was taken eight days after progenitor cells were isolated from an adult female Fisher rat and placed in culture (magnification is 100×).
Figure 3:
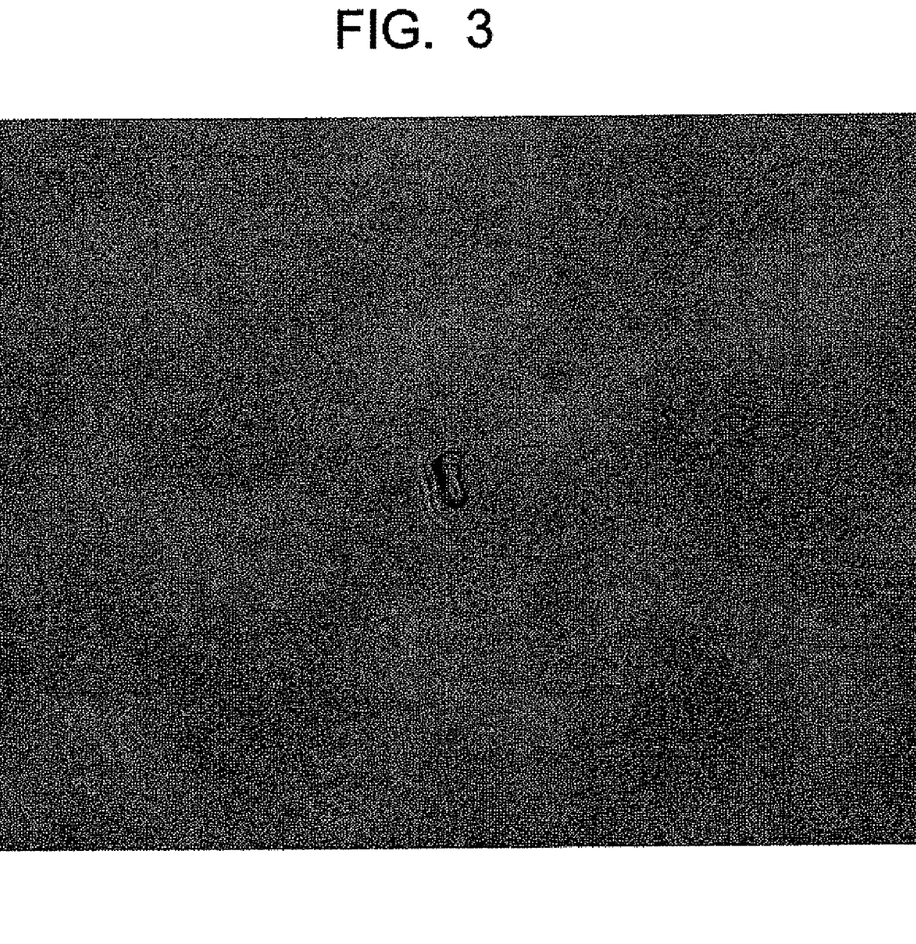
FIG. 3 is a photograph of a primitive hair follicle. The photograph was taken four days after progenitor cells were isolated from an adult female Fisher rat and placed in culture (magnification is 200×).

Progenitor cells isolated and cultured as described herein can differentiate in culture. The progenitor cells have been seen to form an unidentified adnexal skin structure (FIG. 1), a primitive adnexal gland (FIG. 2), and a primitive hair follicle (FIG. 3). Without limiting the invention to cells that differentiate by a particular mechanism, it is believed that progenitor cells may develop along various and committed lineages depending on the cues they receive from neighboring cells; it may be that a concerted and highly interactive process directs the progenitor cell down a particular differentiation pathway.

Example 4

Preparation of a Thermosensitive Hydrogel-Skin Progenitor Cell Composition

A biocompatible, biodegradable, reverse-thermosensitive copolymer gel can be obtained by preparing a 30% weight/volume solution of a PLURONIC™ F127, F68 block copolymer (available from BASF). The solution remains in a liquid state at less than 15° C., and solidifies within 5 to 10 minutes as the temperature is increased to over 15° C. Skin progenitor cells isolated as described above are added to the hydrogel mixture to generate a final cellular density of about $2 \times 10^6$ to $6 \times 10^7$ cells per ml. Such a mixture can be delivered into a permeable support structure.

OTHER EMBODIMENTS

It is to be understood that while the invention has been described in conjunction with the detailed description thereof, that the fore-going description is intended to illustrate and not limit the scope of the invention, which is defined by the scope of the appended claims.

Other aspects, advantages, and modifications are within the scope of the following claims.

What is claimed is:

1. A population of isolated mammalian or avian multipotent spore-like cells (MSLCs) isolated or cultured from skin tissue and which can differentiate into two or more mature skin cell type cells.
   wherein the MSLCs, when first isolated, are approximately one to ten microns in diameter,
   wherein the MSLCs are viable following essentially complete oxygen-deprivation for twenty four hours or more,
   wherein the MSLCs are surrounded by an outer membrane that is rich in glycolipids and mucopolysaccharides so that the MSLCs appear to have one or more dark stripes when viewed by transmission electron microscopy, and
   wherein nucleic acids account for at least about 50% of the volume of each spore-like cell within the population.

2. The MSLC population of claim 1, wherein the cells have an outer coating containing sufficient glycolipids and mucopolysaccharides that the cell appears to have one or more dark stripes when viewed by transmission electron microscopy.

3. The MSLC population of claim 1, wherein the cells are isolated from the skin of a post-natal mammal.

4. The MSLC population of claim 1, wherein the cells are isolated from a culture of spore-like cells isolated from skin by repeated disaggregation of the skin.

5. The MSLC population of claim 1, wherein the cells fail to express nestin.

6. The MSLC population of claim 1, wherein the cells fail to express keratin, tyrosinase, glutamic acid, glutamate, citrulline, tricohyaline, filagrin, epinephrine, norepinephrine, acetylcholine, or melanin granules.

7. MSLC population of claim 1, wherein the cells are isolated from the dermis of a post-natal mammal and, when placed in the vicinity of a skin wound in an animal, expresses a phenotype substantially similar to that of a sympathetic or parasympathetic neuron, or a cell within a sweat gland, a sebaceous gland, or a hair follicle.

8. The MSLC population of claim 1, wherein the cells are isolated from the epidermis of a post-natal mammal and, when placed in the vicinity of a skin wound in an animal, expresses a phenotype substantially similar to that of a melanocyte, a keratinocyte, or a Merkel cell.

9. A method for isolating a multipotent spore-like cell (MSLC population from a post-natal mammal, the method comprising
   passing a piece of skin obtained from the mammal through a series of devices having progressively smaller apertures to isolate a population of MSLCs,
   wherein the MSLCs, when first isolated, are approximately one to ten microns in diameter; and are viable following essentially complete oxygen-deprivation for twenty four hours or more, surrounded by an outer membrane that is rich in glycolipids and mucopolysaccharides, and wherein nucleic acids account for at least about 50% of the volume of each spore-like cell within the population, and wherein the MSLC can differentiate into two or more mature skin cell types.

10. The method of claim 9, wherein the device is a pipette.

11. The method of claim 10, wherein the smallest pipette in the series has an inner bore diameter of approximately 15 microns.

12. The method of claim 9, wherein the device is a filter.

13. The method of claim 9, wherein the filter with the smallest apertures in the series has a pore size of approximately 15 microns.

14. The method of claim 9 wherein the skin is exposed to a digestive enzyme.

15. The method of claim 14, wherein the digestive enzyme is trypsin or collagenase.

16. The method of claim 15, wherein the skin is incubated with approximately 0.05% trypsin at 37° C. for approximately five minutes.

17. A skin construct comprising the MSLC population of claim 1.

18. The skin construct of claim 17, further comprising a support structure.

19. The skin construct of claim 18, further comprising hydrogel, wherein the hydrogel and the MSLC population of claim 1 form a hydrogel-MSLC suspension.

20. A method for generating artificial skin, the method comprising combining hydrogel with the MSLC population of claim 1, to form a hydrogel-MSLC suspension.

21. The method of claim 20, further comprising delivering the hydrogel-cell construct into a permeable, biocompatible support structure.

22. A method of treating damaged skin, the method comprising obtaining a hydrogel-MSLC suspension of claim 19 and applying the suspension to the damaged skin or to an area lying under the damaged skin.

23. The MSLC population isolated by the method of claim 9.

* * * * *